US006174328B1

(12) United States Patent
Cragg

(10) Patent No.: US 6,174,328 B1
(45) Date of Patent: *Jan. 16, 2001

(54) INTRALUMINAL STENT AND GRAFT

(75) Inventor: Andrew H. Cragg, Edina, MN (US)

(73) Assignee: Boston Scientific Technology, Inc., Maple Grove, MN (US)

(*) Notice: Under 35 U.S.C. 154(b), the term of this patent shall be extended for 0 days.

This patent is subject to a terminal disclaimer.

(21) Appl. No.: 09/251,964

(22) Filed: Feb. 16, 1999

Related U.S. Application Data

(63) Continuation of application No. 09/005,654, filed on Jan. 12, 1998, now abandoned, which is a continuation of application No. 08/478,181, filed on Jun. 7, 1995, now Pat. No. 5,766,237, which is a division of application No. 08/344,524, filed on Nov. 23, 1994, now Pat. No. 5,683,448, which is a continuation of application No. 08/025,957, filed on Mar. 3, 1993, now abandoned, which is a continuation-in-part of application No. 07/839,911, filed on Feb. 21, 1992, now Pat. No. 5,405,377.

(51) Int. Cl.⁷ ........................................................ A61F 2/06
(52) U.S. Cl. ........................................ 623/1.16; 623/1.15
(58) Field of Search ................................. 623/1.16, 1.18, 623/1.19

(56) References Cited

U.S. PATENT DOCUMENTS

| 3,868,956 | 3/1975 | Alfidi et al. |
| 3,878,565 | 4/1975 | Sauvage |
| 3,890,977 | 6/1975 | Wilson |

(List continued on next page.)

FOREIGN PATENT DOCUMENTS

| 3918736 A1 | 12/1990 | (DE) |
| 0 145 166 B1 | 6/1985 | (EP) |
| 0 411 118 A1 | 2/1991 | (EP) |
| 0 480 667 A1 | 4/1992 | (EP) |
| 0 508 473 A2 | 10/1992 | (EP) |
| 0 540 290 A2 | 5/1993 | (EP) |
| 1 602 513 | 1/1971 | (FR) |
| 1205743 | 9/1970 | (GB) |
| 2106190A | 4/1983 | (GB) |
| WO 89/02755 | 4/1989 | (WO) |
| WO 91/07928 | 6/1991 | (WO) |
| WO 92/00043 | 1/1992 | (WO) |

OTHER PUBLICATIONS

Dotter et al., "Transluminal Expandable Nitinol Coil Stent Grafting: Preliminary Report," Technical Developments and Instrumentation, *Radiology*, vol. 147, pp. 259–260 (Apr. 1983).
Schetky, "Shape–Memory Alloys," pp. 74–82.
K. Otsuka et al., "Shape–Memory Alloys–Pseudoelasticity," *Metals Forum*, vol. 4, No. 3, pp. 142–152 (1981).
Cragg et al., "Nonsurgical Placement of Arterial Endoprostheses: A New Technique Using Nitinol Wire," *Radiology*, vol. 147, No. 1, pp. 261–263 (Apr. 1983).
Cragg et al., "Percutaneous Arterial Grafting," *Radiology*, vol. 150, No. 1, pp. 45–49 (1984).
T. W. Duerig et al., "An Engineer's Perspective of Pseudoelasticity," pp. 369–393.
Cragg et al., "Stents/Vascular Stents," *Interventional Radiology*, pp. 686–692 (1990).
D. D. Lawrence et al., "Percutaneous Endovascular Graft: An Experimental Evaluation" (Abstract), *Radiology*, May 1987, pp. 357–360.

*Primary Examiner*—John G. Weiss
(74) *Attorney, Agent, or Firm*—Ratner & Prestia

(57) ABSTRACT

An intraluminal stent and graft includes a stent made of a continuous helix of zig-zag wire and loops which connect adjacent apices of the wire. The stent is compressible and self-expandable substantially to a pre-compressed configuration. The device also includes a graft secured to the stent and made of a suitable biocompatible material.

34 Claims, 3 Drawing Sheets

U.S. PATENT DOCUMENTS

| | | |
|---|---|---|
| 3,996,938 | 12/1976 | Clark, III . |
| 4,149,911 | 4/1979 | Clabburn . |
| 4,306,318 | 12/1981 | Mano et al. . |
| 4,425,908 | 1/1984 | Simon . |
| 4,494,531 | 1/1985 | Gianturco . |
| 4,503,569 | 3/1985 | Dotter . |
| 4,512,338 | 4/1985 | Balko et al. . |
| 4,553,545 | 11/1985 | Maass et al. . |
| 4,560,374 | 12/1985 | Hammerslag . |
| 4,577,631 | 3/1986 | Kreamer . |
| 4,580,568 | 4/1986 | Gianturco . |
| 4,649,922 | 3/1987 | Wiktor . |
| 4,655,771 | 4/1987 | Wallsten . |
| 4,665,906 | 5/1987 | Jervis . |
| 4,665,918 | 5/1987 | Garza et al. . |
| 4,681,110 | 7/1987 | Wiktor . |
| 4,729,766 | 3/1988 | Bergentz et al. . |
| 4,732,152 | 3/1988 | Wallstén . |
| 4,733,665 | 3/1988 | Palmaz . |
| 4,739,762 | 4/1988 | Palmaz . |
| 4,762,128 | 8/1988 | Rosenbluth . |
| 4,768,507 | 9/1988 | Fischell et al. . |
| 4,772,264 | 9/1988 | Cragg . |
| 4,776,337 | 10/1988 | Palmaz . |
| 4,787,899 | 11/1988 | Lazarus . |
| 4,800,882 | 1/1989 | Gianturco . |
| 4,820,298 | 4/1989 | Leveen et al. . |
| 4,830,003 | 5/1989 | Wolff et al. . |
| 4,856,516 | 8/1989 | Hillstead . |
| 4,878,906 | 11/1989 | Lindemann et al. . |
| 4,886,062 | 12/1989 | Wiktor . |
| 4,913,141 | 4/1990 | Hillstead . |
| 4,922,905 | 5/1990 | Strecker . |
| 4,969,458 | 11/1990 | Wiktor . |
| 5,019,090 | 5/1991 | Pinchuk . |
| 5,035,706 | 7/1991 | Giantureo et al. . |
| 5,041,126 | 8/1991 | Gianturco . |
| 5,057,092 | 10/1991 | Webster, Jr. . |
| 5,067,957 | 11/1991 | Jervis . |
| 5,078,726 | 1/1992 | Kreamer . |
| 5,078,736 | 1/1992 | Behl . |
| 5,085,635 | 2/1992 | Cragg . |
| 5,104,404 * | 4/1992 | Wolff .................................. 623/1.16 |
| 5,116,365 | 5/1992 | Hillstead . |
| 5,123,917 | 6/1992 | Lee . |
| 5,133,732 | 7/1992 | Wiktor . |
| 5,135,536 | 8/1992 | Hillstead . |
| 5,201,901 | 4/1993 | Harada et al. . |
| 5,242,451 | 9/1993 | Harada et al. . |
| 5,282,824 | 2/1994 | Gianturco . |
| 5,314,472 | 5/1994 | Fontaine . |
| 5,405,377 | 4/1995 | Cragg . |
| 5,456,713 | 10/1995 | Chuter . |
| 5,484,444 | 1/1996 | Braunschweiler et al. . |
| 5,507,767 | 4/1996 | Maeda et al. . |
| 5,545,211 | 8/1996 | An et al. . |
| 5,562,697 | 10/1996 | Christiansen . |

* cited by examiner

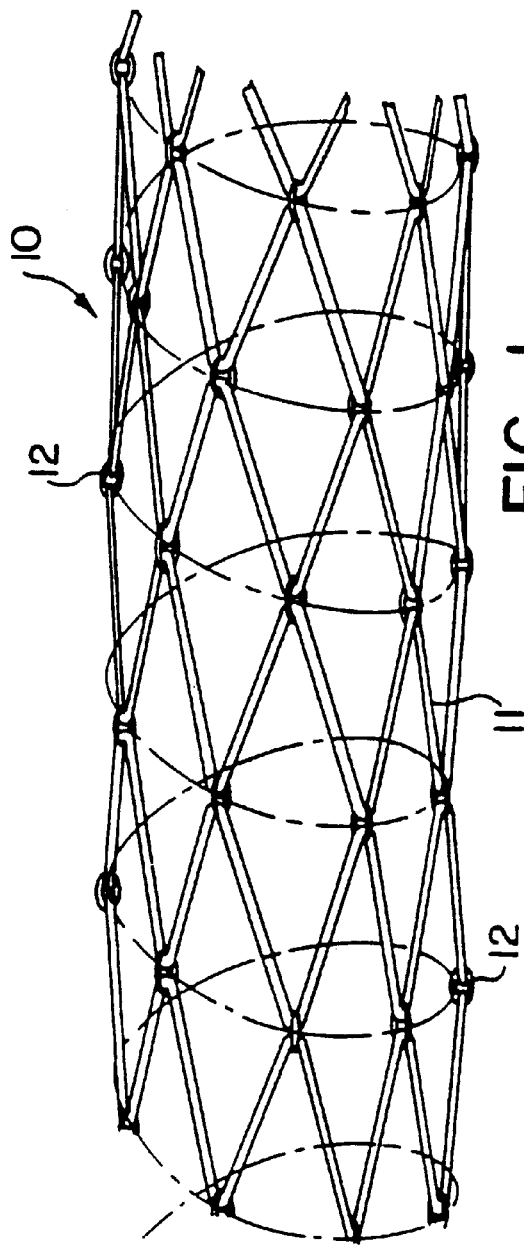
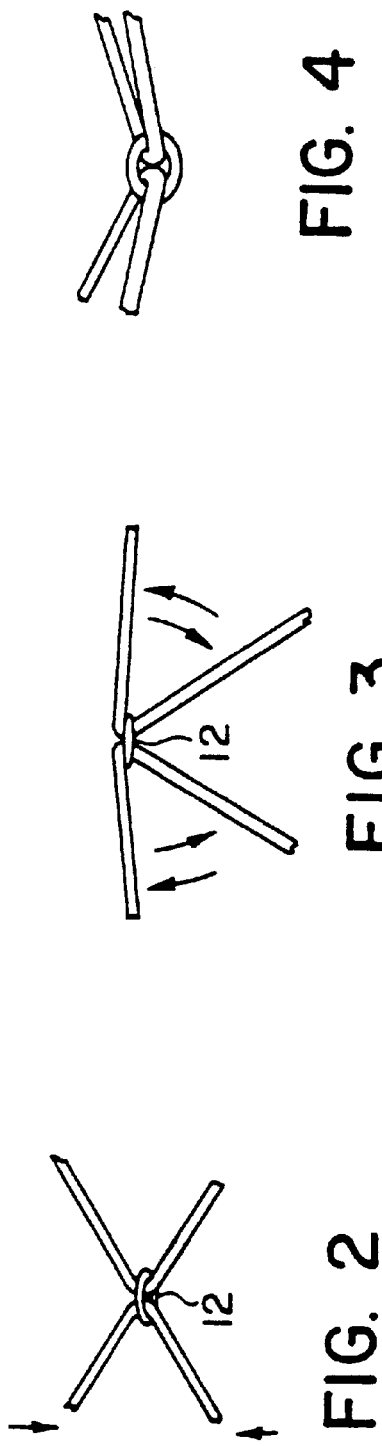

INTRALUMINAL STENT AND GRAFT

This application is a continuation of U.S. application Ser. No. 09/005,654, filed Jan. 12, 1998 now abandon, which is a continuation of U.S. application Ser. No. 08/478,181, filed Jun. 7, 1995 now Pat. No. 5,766,237, which is a division of U.S. Application Ser. No. 08/344,524, filed Nov. 23, 1994 now Pat. No. 5,683,448, which in turn is a continuation of U.S. Application Ser. No. 08/025,957, filed Mar. 3, 1993 now abandon, which in turn is a continuation-in-part of U.S. Application Ser. No. 07/839,911, filed Feb. 21, 1992 now Pat. No. 5,405,377.

BACKGROUND OF THE INVENTION

1. Field of the Invention

The present invention generally relates to a vascular prosthesis, and more particularly to an intraluminal stent which has a flexible and elastic tubular construction with sufficient hoop strength to prevent elastic recoil of balloon-resistant strictures or to produce delayed dilation of those strictures.

2. Description of the Prior Art

The prior art includes a wide variety of intraluminal stents and grafts. For example, Palmaz U.S. Pat. No. 4,733,665 discloses a balloon-expandable intraluminal graft, including an embodiment comprising a wire mesh tube. Intersecting wire members, secured to one another at their intersections by welding, soldering or gluing, form the wire mesh and define a diamond-like pattern. This structure provides a relatively high resistance to radial collapse; but it suffers a number of disadvantages. First it is a rigid structure which cannot easily assume the configuration of a curved vessel which receives it. Second one must use a balloon catheter to expand and implant it. This requirement limits the length of the graft, as does the rigidity.

Other prior stents have more flexible constructions; but they suffer other disadvantages. Wiktor U.S. Pat. No. 4,886,062, for example, discloses a stent which has a relatively flexible construction. This construction includes a deformable wire bent into a zig-zag design and coiled in a spiral fashion. The resulting wire tube has an open configuration with a reduced hoop strength. Each hoop lies essentially isolated from the adjacent hoops and does not obtain substantial support from them. Moreover, the open configuration increases the risk that plaque elements may herniate through the coil. Finally, one must use a balloon catheter to expand and implant it. Thus, the length of the stent cannot exceed the balloon length of available balloon catheters.

The intraluminal stent of the present invention avoids the disadvantages of the prior art stents and grafts. It has sufficient hoop strength to prevent elastic recoil of balloon-resistant strictures. The stent of the present invention has a flexible construction which allows it to follow the curvature of the vessel which receives it. It has an elastic construction which allows implantation without a balloon catheter. This elasticity further allows compression of the structure and recoil upon implantation to produce delayed dilation of the receiving vessel.

SUMMARY OF THE INVENTION

In accordance with an embodiment of the present invention, an intraluminal stent includes a predetermined length of wire having a sinuous or zig-zag configuration and defining a continuous helix with a plurality of connected spirals or hoops. A plurality of loop members connect adjacent apices of adjacent helix hoops. The stent is compressible and self-expandable substantially to the configuration prior to compression.

In accordance with an alternative embodiment of the present invention, an intraluminal stent includes the continuous helix and the plurality of loop members described above. It also includes a prosthetic graft disposed longitudinally of the wire helix within its central opening (or around the wire helix). one or more of the loop members secures the graft to the wire helix. This graft is a flexible, tubular shell which allows the wire helix to contract and recoil.

BRIEF DESCRIPTION OF THE DRAWINGS

For a more complete understanding of this invention one should now refer to the embodiments illustrated in greater detail in the accompanying drawings and described below by way of examples of the invention. In the drawings:

FIG. 1 is a perspective view of the intraluminal stent of the present invention;

FIGS. 2–4 are side elevation views of a suture connection for the stent of FIG. 1;

While the applicant will describe the invention in connection with preferred and alternative embodiments, one should understand that the invention is not limited to those embodiments. Furthermore, one should understand that the drawings are not necessarily to scale. In certain instances, the applicant may have omitted details which are not necessary for an understanding of the present invention.

DETAILED DESCRIPTION OF THE DRAWINGS

Turning now to the drawings, FIG. 1 shows the intraluminal stent of the present invention generally at 10. This stent includes a wire body 11 made out of a predetermined length of wire having a sinuous or zig-zag configuration and defining a continuous helix with a series of connected spirals or hoops. It also includes loop members 12 which connect adjacent apices of adjacent helix hoops to help define the tubular stent. The loop members 12 may connect all or some of the pairs of adjacent apices.

The wire body 11 is an elastic alloy which provides radial elasticity for the stent. Preferably, it is a nitinol alloy which has superior elasticity and fatigue resistance. The wire has a round cross-section; but its cross-section may also be any one of a variety of shapes, e.g., triangular, rectangular, etc. Alternatively, any material of sufficient strength and elasticity and the other properties identified above may form the wire body, including stainless steel, tantalum, titanium, or any one of a variety of plastics.

The loop members 12 connect adjacent apices of adjacent hoops of the wire body 11 so that the adjacent apices abut each other (See FIGS. 2–4). Thus, each hoop receives support from adjacent hoops, increasing the hoop strength of the overall stent structure and minimizing the risk of plaque herniation. The loop members 12 are ligatures of suture material with the ends tied together to form a loop. This material is polypropylene material or any other biocompatible material of sufficient strength. Although sutures are the preferred connecting means, other connecting means such as staples and rings made of metal or plastic may provide the same function.

The stent structure of the present invention allows compression prior to implantation in a human or animal vessel. After implantation, upon release of the compressive force, the stent structure recoils (or self-expands) to its original configuration. Thus, it continues to provide dilating force in the implanted state. The structure provides flexibility which allows the stent to follow the curvature of the vessel which receives it.

Figure 5:
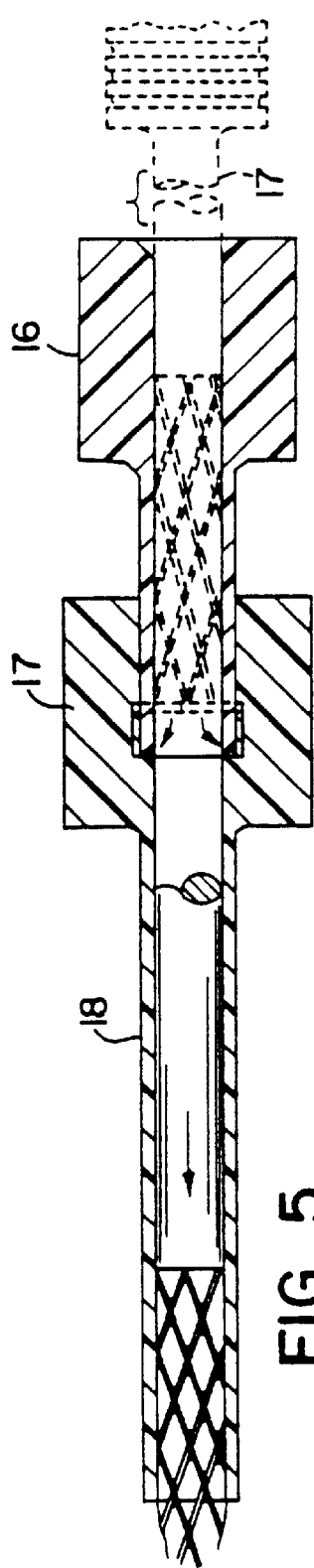
FIG. 5 is a sectional view of the devices used to implant the stent of FIG. 1.
Figure 6:
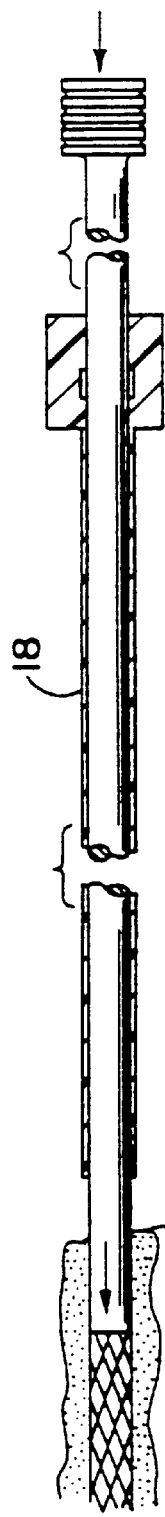
FIG. 6 is a sectional view of the sheath and catheter devices used to implant the stunt, showing the catheter holding the stent in place as the sheath moves out of the body vessel.
Figure 9:
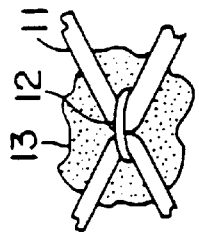
FIG. 9 is a partial perspective view of the stent of FIG. 7, showing a suture connection for the stent.
Figure 8:
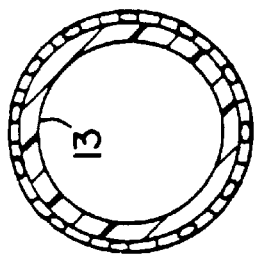
FIG. 8 is a sectional view taken along the line 8—8 in FIG. 7.
Figure 7:
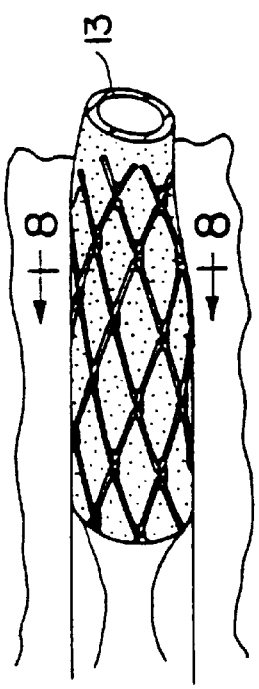
FIG. 7 is a side elevation view of an alternative embodiment of the stent of the present invention.

Turning now to FIGS. 7–9, an alternative embodiment of the present invention includes the wire body and suture connections described above. This alternative also includes a prosthetic graft 13 disposed inside the central opening of the wire body. The graft 13 is a round, open tube made of polytetrafluoroethylene (Pars), dacron or any other suitable biocompatible material. One or more hoop members connect the graft 13 to the wire body 11 as shown in FIG. 9. In place, the graft closes the diamond shaved openings of the stent structure to further minimize plaque herniation and minimize the flow of fluid and cellular elements through the structure.

Alternatively, the graft 13 may lie around the outside of the wire helix. Furthermore, the graft 13 may be co-extensive with the wire helix; or it may be shorter than the wire helix. Finally, the graft 13 may include a plurality of segments disposed within the wire helix or around the outside of the helix.

In one example, the graft 13 is a plain weave fabric construction made in a seamless tubular form on conventional equipment, either a shuttle narrow fabric weaving machine or a needle narrow fabric weaving machine. The tube is of multi filament polyester yarn of 40 denier or less (preferably 20, 30 or 40 denier). The wall thickness of the tube is 0.2 mm or less (preferably 0.1 mm); and it has a water permeability of between 50 and 500 ml/cm$^2$/min at 16 kPa (millimeters of water per square centimeter per minute at a pressure of 16 kPa). The fabric may be coated with a drug substance to reduce permeability, cause local anticoagulation, or reduce cellular infaltration..

Figure 10:
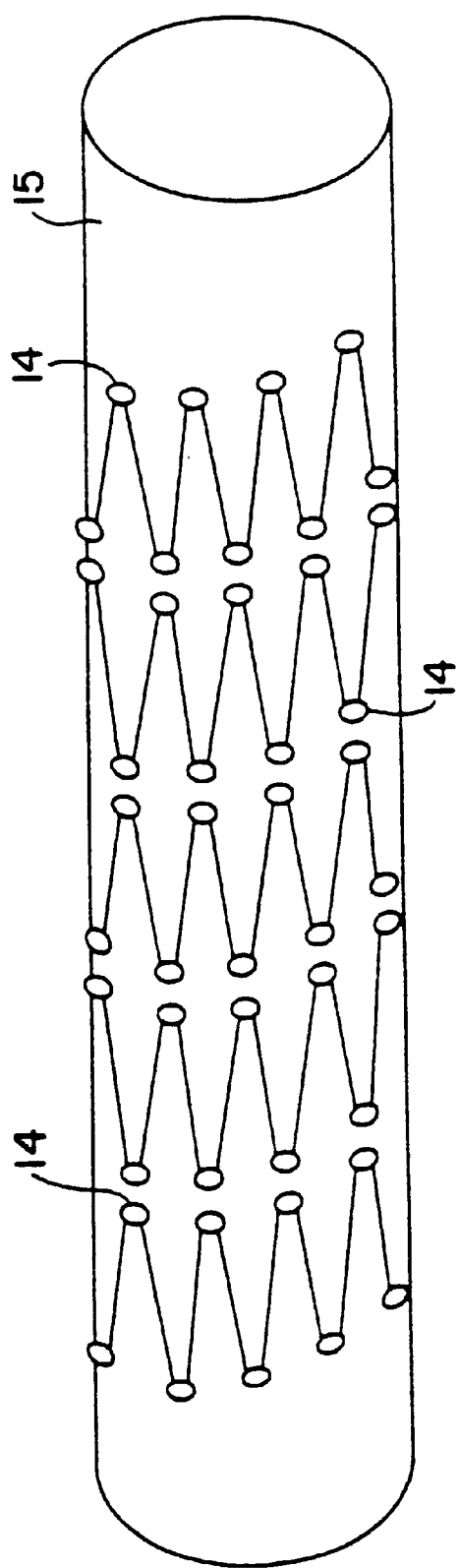
FIG. 10 is a perspective view of the mandrel used to form the wire helix of the present invention.

The method of making the stent of the present invention includes bending a predetermined length of wire in a zig-zag fashion between the pins 14 of the mandrel 15 and around the mandrel, thus forming a helix (See FIG. 10). The next step includes removing the helix from the mandrel by removing the pins and sliding the helix off the mandrel. The process further includes connecting adjacent apices of adjacent helix hoops. A fabricator makes each connection by placing a ligature of suture material (or any other suitable material) around the wire segments which define two adjacent apices and tying the ends of the ligature together to form a loop. In applications in which the wire body is nitinol wire, the process includes securing the ends of the wire to the mandrel and annealing the wire to a predetermined temperature (and thus imparting a thermal memory for the annealed shape) before removing the helix from the mandrel.

The method of implanting the stent and graft of the present invention includes compressing it and placing it into the central bore of an introducing device 16. The next step includes coupling the device 16 with the hub 17 of a sheath 18 which extends to the implantation location. The next step involves using a catheter 19 to push the compressed stent to the predetermined location and to hold the stent at the location with the catheter, and then removing the sheath. The final step involves removal of the catheter to allow the stent to recoil.

In applications in which the wire body is a nitinol metal, a user reduces the diameter of the stent by first cooling it, e.g., by submerging it in ice water. This cooling places the nitinol in a martensitic phase and facilitates manual reduction of the diameter and insertion of the stent in the central bore of the device 16. The device 16 and the sheath 18 restrain the stent until deployment in a predetermined location. At that location in a subject's body, body fluids warm the nitinol and place it in an austenitic phase which is the stable phase of this metal and which corresponds to a fully opened or expanded configuration of the stent (to its original annealed diameter).

While the above description and the drawings illustrate one embodiment and an alternative, one should understand, of course, that the invention is not limited to those embodiments. Those skilled in the art to which the invention pertains may make other modifications and other embodiments employing the principals of this invention, particularly upon considering the foregoing teachings. For example, one may use a deformable material to construct the wire body 11 of the stent and then us, a balloon catheter to deploy it. The applicant, therefore, by the appended claims, intends to cover any modifications and other embodiments which incorporate those features which constitute the essential features of this invention.

What is claimed:

1. A stent comprising a tubular member having hoops aligned along the axis of said tubular member, each of said hoops comprising a series of sinusoidal or zig-zag elements including apices alternatingly pointing in opposite directions along the axis of the stent with at least some of said apices of one hoop axially abutting oppositely pointed apices of an adjacent hoop and being connected thereto by separate connecting members.

2. A stent according to claim 1, wherein said tubular member is made from a shape memory alloy.

3. A stent according to claim 2, wherein said shape memory alloy is nitinol.

4. A stent according to claim 1, wherein said connecting member is a suture material.

5. A stent according to claim 4, wherein said suture material is polypropylene.

6. A stent according to claim 1, wherein all of said apices of one hoop axially abut oppositely pointed apices of an adjacent hoop and are connected thereto.

7. A stent according to claim 1, further comprising a tubular graft member secured to said tubular member with at least one said connecting member.

8. A stent according to claim 7 wherein said graft member lies within said tubular member.

9. A stent comprising a tubular member having a plurality of hoops aligned along the axis of said tubular member but not overlapping one another, each of said hoops comprising a series of axially aligned zig-zag elements including apices that point in opposite directions along the axis of the stent, axially adjacent hoops having axially abutting opposite oppositely pointed apices, wherein at least some of said axially abutting apices are connected to one another by a plurality of separate connecting members.

10. A stent according to claim 9, wherein said stent is comprised of a shape memory material.

11. A stent according to claim 10, wherein said shape memory material is nitinol.

12. A stent according to claim 9, wherein said stent is comprised of an elastic material.

13. A stent according to claim 12, wherein said elastic material is stainless steel.

14. A stent according to claim 9, wherein at least one zig-zag element in each hoop is a continuation of a zig-zag element of an adjacent hoop.

15. A method of reinforcing a body vessel using a tubular sheath disposed between an entry location in a body and an implantation location, said method comprising the steps of:
   a. providing stent comprising a tubular member having a compressed configuration and a self-expandable expanded configuration having a plurality of hoops aligned along the axis of said tubular member but not overlapping one another, each of said hoops comprising a series of axially aligned sinusoidal or zig-zag elements including apices alternatingly pointing in opposite directions along the axis of the stent, wherein at least some of said sinusoidal or zig-zag elements are connected to axially abutting, oppositely pointed apices of the zig-zag elements of an adjacent hoop by a plurality of separate connecting members;
   b. compressing the stent into its compressed configuration;
   c. inserting the compressed stent into the tubular sheath;
   d. delivering the compressed stent through the tubular sheath to the implantation location;
   e. withdrawing the sheath while holding the stent at the implantation location within the vessel and expanding the stent within the implantation location as the sheath is withdrawn by permitting the self-expandable stent, as the constraint of the sheath is removed, to return to said expanded configuration;
   whereby the stent is securely disposed in the implanted state against said body vessel.

16. A method according to claim 15, wherein said stent is comprised of a shape memory material.

17. A method according to claim 16, wherein said shape memory material is nitinol.

18. A method according to claim 15, wherein said stent is comprised of an elastic material.

19. A method according to claim 18, wherein said elastic material is stainless steel.

20. A method according to claim 15, wherein at least one zig-zag element in each hoop is a continuation of a zig-zag element of an adjacent hoop.

21. A stent comprising a tubular member having a plurality of hoops aligned along the axis of said tubular member, each of said hoops comprising a plurality of elongate elements, said elements being joined to one another and forming apices that point in a directions along the axis of the stent, said apices axially abutting oppositely pointed apices of adjacent hoops, wherein at least some of said hoops are connected to one another at said axially abutting oppositely pointed apices, each of said connected axially abutting oppositely pointed apices being connected by a separate connecting member.

22. A stent, as recited in claim 21, wherein said elongate elements are composed of nitinol.

23. A stent, as recited in claim 22, including a tubular graft, wherein sail stent structure includes diamond-shaped openings and said graft covers said openings.

24. A stent, as recited in claim 21, said elements forming diamond shaped openings, said stent including a tubular graft and one or more loop members connecting said graft to said elements, said graft covering said diamond shaped openings.

25. A stent, as recited in claim 24, wherein said stent elongate elements are composed of nitinol.

26. A stent comprising a tubular member having a plurality of hoops aligned along the axis of said tubular member, each of said hoops including a plurality of elongate elements joined to one another and forming apices that point in a direction along the axis of the stent, the apices of adjacent hoops abutting oppositely pointed apices of an adjacent hoop, and individual connecting members attaching adjacent hoops at a plurality of said abutting apices.

27. A stent, as recited in claim 26, wherein said elongate elements are composed of nitinol.

28. A stent, as recited in claim 27, including a tubular graft, wherein said stent structure includes diamond-shaped openings and said graft covers said openings.

29. A stent, as recited in claim 26, said elements forming diamond shaped openings, said stent including a tubular graft and one or more loop members connecting said graft to said elements, said graft covering said diamond shaped openings.

30. A stent, as recited in claim 29, wherein said stent elongate elements are composed of nitinol.

31. A stent, as recited in any of claims 1, 3, 9, 14, 21 and 26, further comprising a tubular graft disposed within the central opening of said stent and attached thereto.

32. A stent, as recited in claim 31, wherein said stent structure includes diamond-shaped openings and said graft covers said openings.

33. A stent, as recited in any of claims 1, 3, 9, 14, 21 and 26, further comprising a tubular graft surrounding said stent and attached thereto.

34. A stent, as recited in claim 33, wherein said stent structure includes diamond-shaped openings and said graft covers said openings.

* * * * *